(12) United States Patent
Takeuchi et al.

(10) Patent No.: US 6,226,080 B1
(45) Date of Patent: *May 1, 2001

(54) METHOD FOR DETECTING DEFECT OF TRANSPARENT BODY, METHOD FOR PRODUCING TRANSPARENT BODY

(75) Inventors: Yukihisa Takeuchi, Aichi-Pref.; Tsutomu Nanataki, Toyoake; Iwao Ohwada, Nagoya; Kei Sato, Tokai, all of (JP)

(73) Assignee: NGK Insulators, Ltd., Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/274,936

(22) Filed: Mar. 23, 1999

(30) Foreign Application Priority Data

Mar. 24, 1998 (JP) .................................................. 10-075962
Feb. 26, 1999 (JP) .................................................. 11-050914

(51) Int. Cl.[7] .................................................. G01N 21/17
(52) U.S. Cl. .................................. 356/239.1; 356/239.8
(58) Field of Search ........................... 356/239.1, 239.2, 356/239.7, 239.8, 237.1; 250/223 B, 227.23, 227.21

(56) References Cited

U.S. PATENT DOCUMENTS

| H376 | * | 12/1987 | Bremer | ............................ 356/239.2 |
|---|---|---|---|---|
| 3,985,454 | * | 10/1976 | Fletcher et al. | ................... 356/239.1 |
| 4,808,813 | * | 2/1989 | Champetier | ........................ 356/239.1 |
| 5,196,901 | * | 3/1993 | Champetier | ........................ 356/237.3 |
| 5,355,213 | * | 10/1994 | Dotan | ................................ 356/239.7 |
| 5,517,301 | * | 5/1996 | Dave | ................................ 356/237.1 |

FOREIGN PATENT DOCUMENTS

| 58-158920 | 9/1983 | (JP) . |
|---|---|---|
| 4-96053 | 8/1992 | (JP) . |
| 10-78549 | 3/1998 | (JP) . |

* cited by examiner

*Primary Examiner*—Hoa Q. Pham
(74) *Attorney, Agent, or Firm*—Burr & Brown

(57) ABSTRACT

Defect of an acrylic plate is detected such that a light beam, which dominantly includes non-parallel rays not parallel to a principal surface of the acrylic plate, is introduced through a side surface formed substantially perpendicularly to the principal surface of the acrylic plate. In this arrangement, transmitted light, which is obtained through the principal surface of the acrylic plate on the basis of the defect, is detected by using any one of or both of a light-receiving device with its light-receiving surface arranged and directed substantially in parallel to the principal surface of the acrylic plate and a light-receiving device with its light-receiving surface arranged and directed substantially perpendicularly to the principal surface of the acrylic plate. Thus, the defect of the acrylic plate is quantitatively detected by measuring the amount of light of the transmitted light. Accordingly, an identical optical system can be used to perform the detection of, for example, the surface scratch of the acrylic plate as well as the bubble and the foreign matter in the acrylic plate simultaneously with the detection of the defect such as the bend and the waviness of the acrylic plate itself.

23 Claims, 14 Drawing Sheets

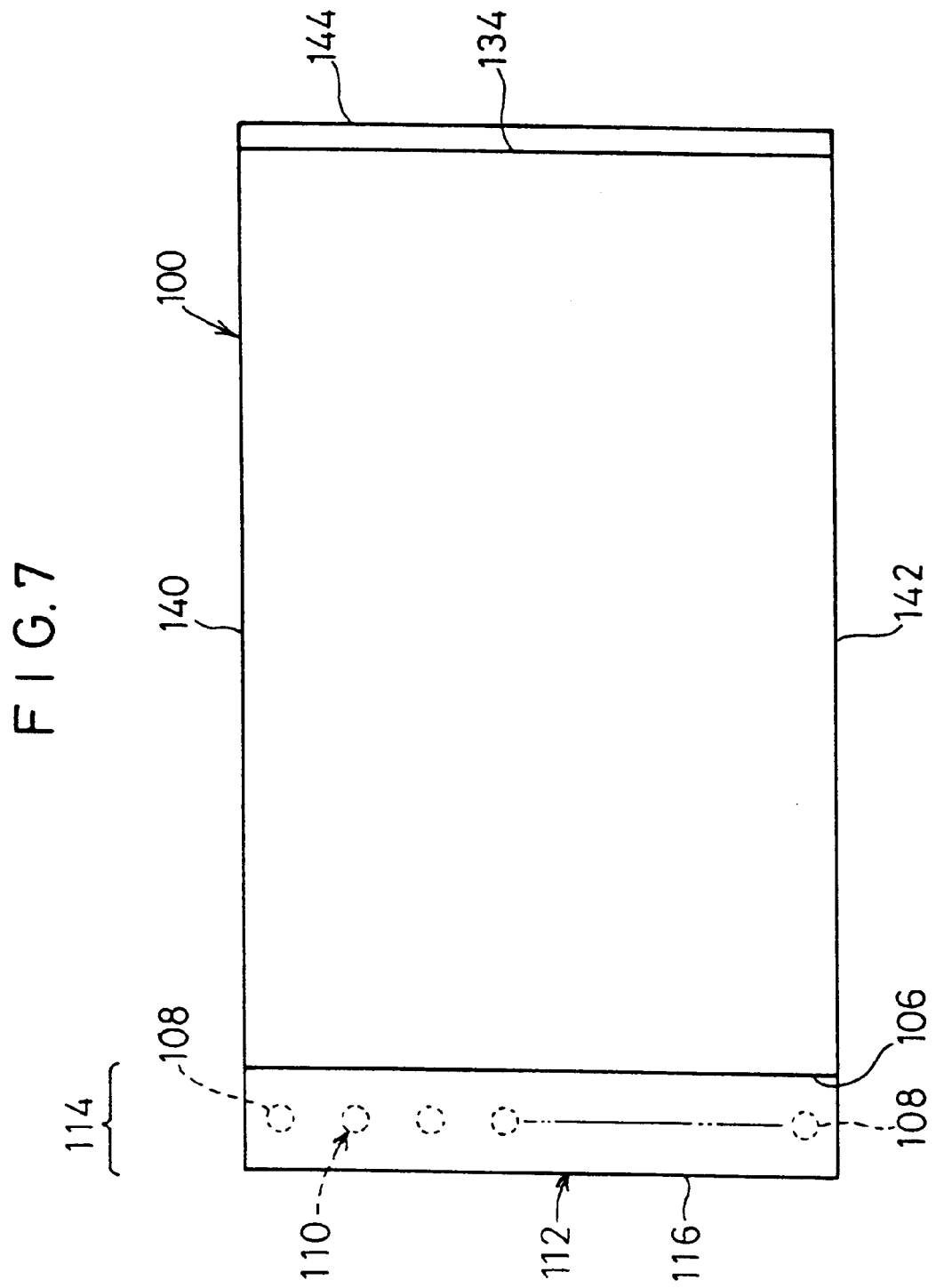

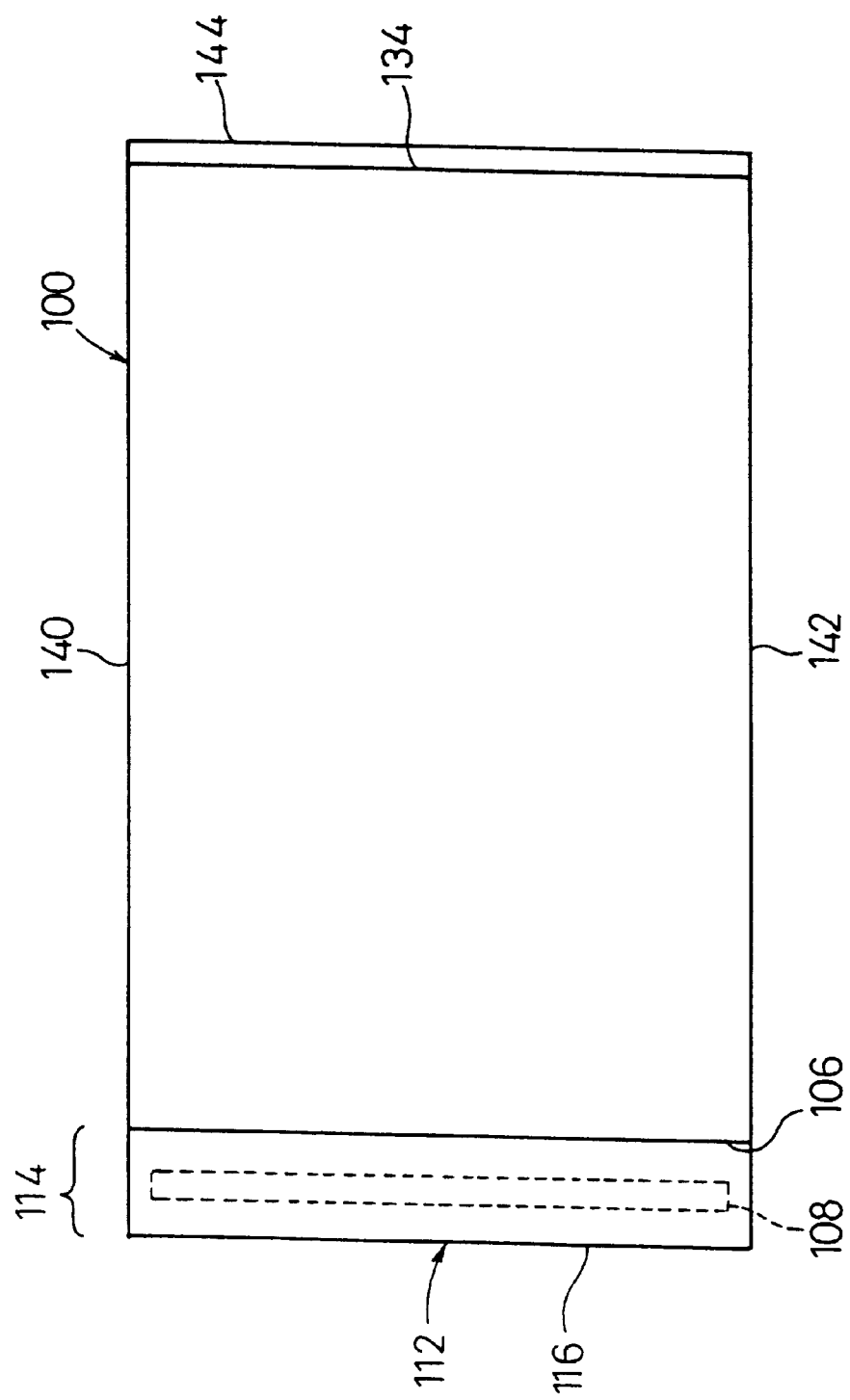

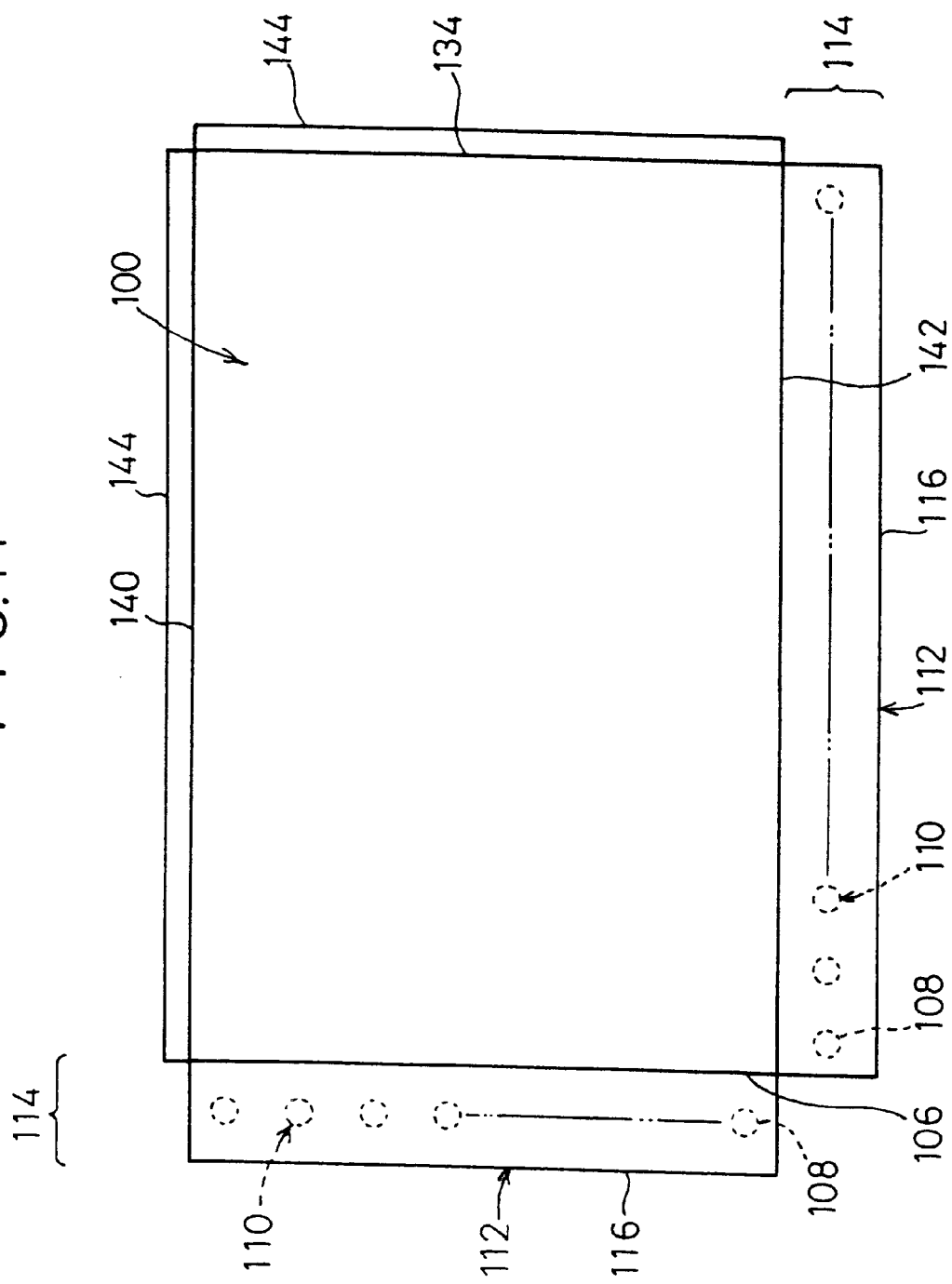

F I G.15
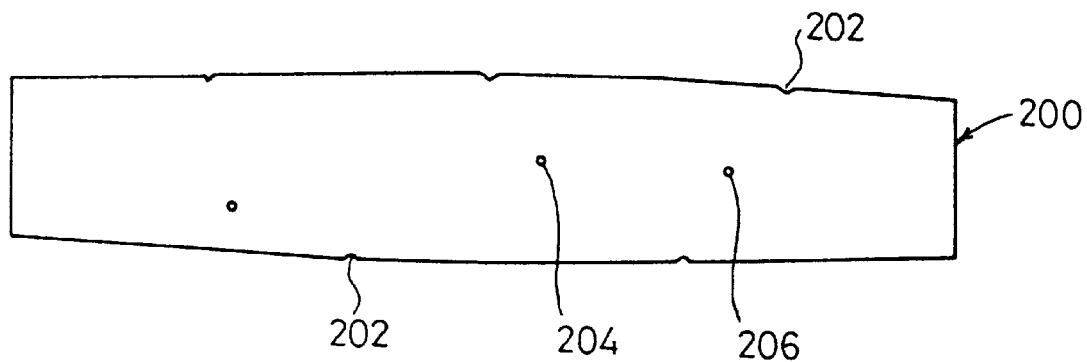

METHOD FOR DETECTING DEFECT OF TRANSPARENT BODY, METHOD FOR PRODUCING TRANSPARENT BODY

BACKGROUND OF THE INVENTION

1. Field of the Invention

The present invention relates to a method for detecting a defect of a transparent body and a method for producing a transparent body. In particular, the present invention relates to a method for detecting a defect of a transparent body, which is preferably used to detect the defect such as the bubble, the foreign matter, and the surface scratch existing, for example, in an acrylic plate, as well as the bend, the waviness, and the warpage of the acrylic plate itself. The present invention also relates to a method for producing a transparent body, in which an obtained result of detection of the defect is sent in a feedback manner to a production line for the transparent body to make changes to the production of the transparent body.

2. Description of the Related Art

Those hitherto known as the display include, for example, cathode ray tubes (CRT) and liquid crystal display apparatuses.

The material, which is often used for an optical guide plate of such a display, is glass or a transparent material, because it is necessary to totally reflect, within the optical guide plate, the light introduced from a light source.

When the optical guide plate is composed of glass, the following problems occur. That is, the weight of the optical guide plate is large when the display surface has a large size. Further, the price of glass is expensive.

In order to solve the problems as described above, an acrylic plate is also used as a material for the optical guide plate.

However, as shown in FIG. 15, when an optical guide plate is produced by using an acrylic plate 200, a scratch 202 tends to be formed on its surface. Further, for example, a bubble 204 and a foreign matter 206 sometimes appear in the acrylic plate 200. Furthermore, the flatness is occasionally lost due to any bend or waviness of the acrylic plate 200 itself.

Because of the circumstances as described above, an inspection is made whether any defect as described above is present or absent by means of visual observation effected by human eyes, during the inspection step for the products of the acrylic plates 200. However, such a process is not necessarily efficient.

On the other hand, a technique for inspecting defect of a transparent body has been disclosed in which a light beam originating from a light source is radiated onto a plate member to inspect the plate member for its defect or the like (see, for example, Japanese Laid-Open Patent Publication No. 58-158920). An apparatus for inspecting the defect described in this document is operated as follows for the foreign matter and the scratch on the surface. That is, the light beam originating from the light source regulated by a slit in the radiation direction is radiated in parallel to a transparent body such as a glass mask for photolithography (in parallel to a principal surface of the transparent body), and scattered light concerning the foreign matter and the scratch on the surface is received by using a light-receiving unit so that the inspection is made for the presence or absence of the foreign matter and the surface scratch directed to the mask aperture.

However, in the case of the conventional apparatus for inspecting the defect, it is required to radiate the parallel light beam onto the plate member, and hence it is necessary to newly provide any optical system for producing the parallel light beam from the light supplied, for example, from a point light source. Therefore, it is feared that the system may be complicated. Further, a problem arises in that the positional control to radiate the parallel light beam onto the entire transparent body is difficult to implement.

When the parallel light beam is used, the following inconvenience arises. That is, it is impossible to detect any foreign matter or the like adhering to the surface of the plate member if the slit is located on the side surface of the plate member. When the surface of the foreign matter existing in the plate member is a mirror surface, the reflected light of the parallel light beam is not transmitted to the side of the principal surface depending on the position and the angle thereof. The reflected light is transmitted toward the side surface of the transparent body, and it cannot be detected by the light-receiving unit which is installed over the principal surface of the transparent body.

As understood from the principle of detection, the conventional technique described above makes it possible to detect a surface scratch and the foreign matter existing at the inside of the transparent body. However, the conventional technique fails to detect, for example, the bend and the waviness of the transparent body itself.

Further, in the conventional technique, the parallel light beam is introduced via a slit into a measurement space in which the transparent body is installed. For this reason, in order to perform the detection of the bubble, the foreign matter and the like existing in the transparent body and the detection of the scratch existing on the surface, it is necessary to move the slit in the thickness direction of the transparent body. Therefore, it is impossible to simultaneously perform the two detection processes described above. When the transparent body has a large thickness, a new problem arises in that the detection requires a lot of time and labor.

SUMMARY OF THE INVENTION

The present invention has been made taking the foregoing problems into consideration, an object of which is to provide a method for detecting a defect of a transparent body, which makes it possible to quantitatively and accurately detect, for example, a surface scratch, a bubble, and foreign matter in the transparent body, which are the defect of the transparent body.

Another object of the present invention is to provide a method for detecting a defect of a transparent body, which makes it possible to quantitatively and accurately detect, for example, the bend and the waviness of the transparent body itself.

Still another object of the present invention is to provide a method for detecting a defect of a transparent body, which makes it possible to perform a detection of a surface scratch of the transparent body, a bubble, foreign matter or the like in the transparent body simultaneously with the detection of the defect such as the bend and the waviness of the transparent body itself by using an identical optical system.

Still another object of the present invention is to provide a method for producing a transparent body, which makes it possible to produce the transparent body having fewer defects and having a high quality by sending, in a feedback manner to a production line for the transparent body, a result of the detection of defect obtained by the method for detecting defects of the transparent body to be achieved as described above.

The present invention lies in a method for detecting a defect of a transparent body, comprising the step of introducing a light beam predominantly including non-parallel rays which are not parallel to a principal surface of the transparent body, through at least one side surface which is formed substantially perpendicularly to the principal surface of the transparent body to detect the defect of the transparent body. The transparent body includes, for example, an acrylic plate to be used as an optical guide plate for the optical application such as the display.

Explanation will now be made for the optical path obtained when the light beam predominantly including the nonparallel rays is introduced into the transparent body, and for the principle of detection of the defect of the transparent body.

With reference to FIG. 1, when a light beam is transmitted from the transparent body 10 having a large refractive index (absolute refractive index) into the air 12 having a small refractive index, if the angle of incidence $\theta_r$ is gradually increased, the angle of refraction $\theta_r$ is increased corresponding thereto. However, when the angle of refraction $\theta_r$ arrives at 90°, the light beam is not transmitted (see an optical path indicated by a solid line "b" in FIG. 1, but the optical path is actually overlapped with the interface between the transparent body 10 and the air 12, but is depicted with deviation for the convenience of explanation). When the angle of incidence $\theta_i$ is further increased, the light beam is totally reflected in the transparent body 10 (see an optical path indicated by a dashed line "c" in FIG. 1).

The corresponding angle of incidence $\theta_i$, which is obtained when the angle of refraction $\theta_r$ is 90°, is called the "critical angle $\theta_i$", and it can be determined from the expression of the law of refraction represented by $\sin\theta_i/\sin\theta_r = n_2/n_1$, wherein $n_1$ and $n_2$ represent the refractive indexes of the transparent body 10 and the air 12 respectively. Assuming that the refractive index $n_1$ of the transparent body 10 has a value of 1.49, that the refractive index $n_2$ of the air 12 has a value of 1.00, and $\sin\theta_i = \sin\theta_r = 1$ the critical angle $\theta_i'$ is 42.2°.

With reference to FIG. 2, when a light beam 18a from a light source 16 is radiated in a direction opposite to the above at an angle of incidence of about 90° into a side surface 14 which is formed perpendicularly to the principal surface of the transparent body 10, the angle of refraction $\theta_i$ in the transparent body 10 has a value which is near to the critical angle of 42.2°. When the light beam 18a arrives at a principal surface 20 of the transparent body 10, the angle of incidence $\theta_2$ with respect to the air 12 has a value which is near to 47.8° (=90−$\theta_1$).

Since the value of the angle of incidence $\theta_2$ is greater than the critical angle of 42.2°, the light beam 18a behaves as a reflected light beam 18b without producing any transmitted light 18c provided that the principal surface 20 of the transparent body 10 is a completely smooth surface. However, if any bubble 22 or the like exists in the transparent body 10, then the light beam 18b is scattered, and the transmitted light 18c is produced. Accordingly, the defect such as the bubble 22 can be detected by detecting the transmitted light 18c by using a light-receiving device 24.

As for the transmitted light 18c, if the existing size of the bubble 22 or the like is large (or if many bubbles 22 exist), the scattering is caused to a greater extent. Therefore, the light amount of the transmitted light is also increased. The term "existing amount of the bubble 22 or the like" resides in a concept to indicate the size of each bubble 22 and the number of bubbles 22 or the like.

Therefore, the existing size of the defect can be quantitatively detected depending on the light amount measured by the light-receiving device 24.

In this case, if the light beam 18a from the light source 16 is introduced into the side surface 14 formed perpendicularly to the principal surface 20 of the transparent body 10, at the angle of incidence within a range of 0° to 90°, the value of the angle of incidence $\theta_2$ necessarily exceeds the critical angle. If the principal surface 20 of the transparent body 10 is a completely smooth surface, all of the light beam 18a behaves as the reflected light beam 18b. Therefore, it is possible to use an arbitrary angle for the angle of incidence into the side surface 14 of the transparent body 10. It is preferable that the position of the light-receiving surface of the light-receiving device 24 is directed substantially in parallel to the principal surface 20 of the transparent body 10. However, it is also allowable that the light-receiving surface is not parallel, and has an appropriate angle. The method for introducing light as described above is effective if the refractive index of the transparent body 10 is larger than $\sqrt{2}$.

On the other hand, as shown in FIG. 3, for example, when the transparent body 10 has a wavy surface 30, if the light beam 18a is radiated from the light source 16 in the same manner as described above, then the angle of incidence $\theta_3$ at the corresponding position is smaller than the angle of incidence $\theta_4$ at the smooth surface. When the angle of incidence $\theta_3$ is smaller than the critical angle, namely when the wavy surface 30 forms an angle of inclination exceeding, for example, 5.6°, the transmitted light 18c is produced as shown in FIG. 3.

The transmitted light 18c is detected by using the light-receiving device 24 which has its light-receiving surface directed substantially perpendicular to the principal surface 20 of the transparent body 10 so as to respond to the transmitted light 18c which has its optical path extending approximately in parallel to the principal surface 20 of the transparent body 10. Thus, it is possible to detect the defect of the wavy surface 30 of the transparent body 10 by means of the convenient method. As shown in FIG. 4, this method makes it possible to detect not only the wavy surface 30 as described above but also the loss of flatness due to, for example, the surface scratch 32 and the warpage of the transparent body 10. Also in this case, defect such as the waviness, the surface scratch, and the warpage (existing amount of the defect) can be quantitatively detected by measuring the light amount of the transmitted light 18c by using the light-receiving device 24.

Further, the light-receiving device may be based on the combination of at least one light-receiving device with its light-receiving surface which is arranged and directed substantially in parallel to the principal surface of the transparent body, and at least one light-receiving device with its light-receiving surface which is arranged and directed substantially perpendicular to the principal surface of the transparent body. Thus, the existing amount of the defect of the transparent body can be detected quantitatively and efficiently.

As described above, the non-parallel ray referred to in the present invention indicates light rays which are not parallel to the principal surface of the transparent body. Specifically, for example, as shown in FIG. 5, the non-parallel ray refers to a group of light fluxes (light flux group) introduced into the side surface of the transparent body 10 at various angles. For example, when one imaginary point P is assumed at the inside of the transparent body 10, the non-parallel ray indicates a group of various rays (light flux group) passing through the point P at different angles of incidence respectively. It is a matter of course that the point P is imaginary. Other light flux groups, which do not pass through the point P, can be also defined as the non-parallel ray.

The group of light fluxes of the non-parallel rays, which are introduced into the transparent body in the direction substantially parallel to the side surface, are reflected many times in the transparent body. Accordingly, the detection sensitivity is improved for any of the defects including, for example, foreign matter, the bubble, the scratch, the waviness, and the warpage existing in the transparent body and on the front and back surfaces thereof.

If the light flux group introduced into the transparent body includes only the light flux group introduced substantially in parallel to the side surface as described above, it is impossible to introduce a sufficient amount of light into the middle portion of the transparent body, because the light is transmitted by the defect in the transparent body especially when the defect is detected for the-transparent body having a large size.

However, the light introduced into the transparent body in the present invention is not limited to such a light flux group as described above. In addition thereto, there are also a group of light fluxes parallel to the principal surface of the transparent body (the fluxes being introduced up to portions separated far from the light source). Therefore, the shortage in light amount is not caused, which would be otherwise caused as described above. Accordingly, it is possible to introduce a substantially constant amount of light over the entire transparent body. Thus, it is possible to improve the sensitivity of the defect detection for the entire transparent body. In this arrangement, the sufficient ratio of the non-parallel ray with respect to the introduced light is not less than 50%. More preferably, the ratio of the non-parallel ray is not less than 90%.

As described above, the method for detecting the defect of the transparent body according to the present invention is a defect-detecting method which utilizes the total reflection at the front and back surfaces of the transparent body, making it possible to simultaneously detect defects including, for example, foreign matter, the bubble, the scratch, the waviness, and the warpage existing in the transparent body and on the front and back surfaces thereof. Further, it is unnecessary to prepare any parallel light beam. Therefore, it is possible to realize the defect detection by using the simple system construction.

In other words, the light beam, which predominantly includes the non-parallel rays, is introduced through at least one side surface formed substantially perpendicular to the principal surface of the transparent body. Thus, the existing size of the defect of the transparent body can be highly accurately detected by means of the convenient method.

Preferably, the method further comprises the steps of allowing a scattering member to make contact with a principal surface of the principal surfaces of the transparent body disposed on a side opposite to a side on which the light-receiving device is arranged, at a position opposing the light-receiving surface of the light-receiving device to detect transmitted light on this condition by using the light-receiving device so that an obtained detection level is used as a reference level; detecting transmitted light by using the light-receiving device when the scattering member is removed so that an obtained detection level is used as an observation level; and quantitatively detecting an existing size of the defect of the transparent body on the basis of a ratio between the reference level and the observation level.

In this arrangement, the defect of the transparent body can be detected with a certain sensitivity regardless of the detection position. Thus, it is possible to accurately recognize the distribution of the existence of defect over the entire transparent body.

The light source is not specifically limited provided that it radiates the light beam dominantly including the non-parallel rays. Those usable as the light source include, for example, fluorescent tubes, metal halide lamps, xenon lamps, halogen lamps, incandescent lamps, and LED's.

The light beam, which predominantly includes the non-parallel rays, is not necessarily introduced through one position on the side surface disposed substantially perpendicular to the principal surface of the transparent body. In order to introduce the light in an amount as large as possible, the light is preferably introduced into the transparent body through the entire end surface.

The shape of the transparent body is not specifically limited. That is, the principal surface of the transparent body may have a circular, rectangular, elliptic, or polygonal planar configuration. Alternatively, the planar configuration may be a combination of these configurations. However, it is necessary that the side surface, through which the light beam is introduced, is substantially perpendicular to the principal surface. Desirably, it is preferable that all of the side surfaces of the transparent body are substantially perpendicular to the principal surface of the transparent body.

In the defect-detecting method described above, it is also preferable that the light beam from the light source is introduced through the side surface of the transparent body, predominantly including the non-parallel rays by the aid of a light source side reflector installed on a side of the light source. In this arrangement, it is preferable that an angle of incidence of the light beam from the light source with respect to the side surface of the transparent body is controlled by using the light source side reflector.

Further, it is also preferable that the reflector is arranged for a side surface of the side surfaces of the transparent body other than the side surface for which the light source is installed.

In other words, the reflector may make contact with the side surface of the transparent body, or it may be separated therefrom. Alternatively, the reflector may be constructed to cover the light source.

In another aspect, the present invention lies in a method for producing a transparent body by polymerizing a monomer by the aid of a catalyst, comprising the steps of introducing a light beam predominantly including non-parallel rays which are not parallel to a principal surface of the produced transparent body, through at least one side surface which is formed substantially perpendicular to the principal surface of the transparent body to detect the defect of the transparent body, and sending a result of the detection of the defect to a production line for the transparent body in a feedback manner so that the result is utilized to produce the transparent body.

That is, the defect, which may exist in the produced transparent body, is detected highly accurately by utilizing the method for detecting the defect of the transparent body according to the present invention. The result of the detection of the defect is sent to the production line for the transparent body using feedback so that the result is utilized to produce the transparent body. Accordingly, it is possible to produce the transparent body having a high quality and involving fewer defects.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 7 shows a planar arrangement concerning the method for detecting the defect according to the embodiment of the present invention;

FIG. 9 shows a planar arrangement of an embodiment based on the use of a cylindrical fluorescent tube as a light source;

FIG. 11 shows a planar arrangement of the method for detecting the defect according to another embodiment;

FIG. 15 illustrates the state of occurrence of the defect such as the internal bubble in the acrylic plate.

DESCRIPTION OF THE PREFERRED EMBODIMENTS

Explanation will be made below with reference to FIGS. 6 to 13 for illustrative embodiments in which the method for detecting the defect of the transparent body according to the present invention is applied to a method for detecting a defect of an acrylic plate (hereinafter simply referred to as "method for detecting the defect according to the embodiment").

Figure 6:
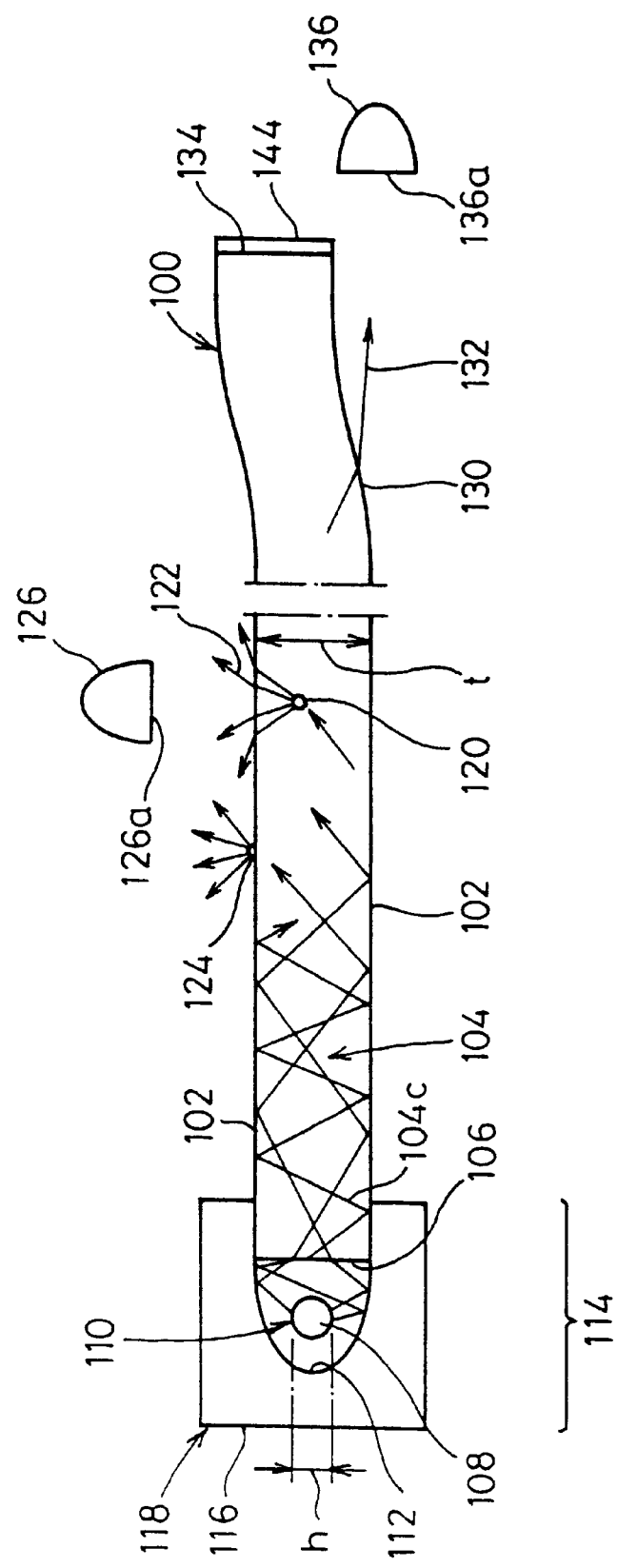
FIG. 6 shows an arrangement as viewed from a side, for an illustrative embodiment in which the method for detecting the defect of the transparent body according to the present invention is applied to a method for detecting defect of an acrylic plate (hereinafter simply referred to as "method for detecting the effect according to the embodiment")

At first, the method for detecting the defect according to the first embodiment is constructed as shown in FIG. 6. That is, a light beam 104, which predominantly includes nonparallel rays not parallel to a principal surface 102 of an acrylic plate 100, is introduced through at least one side surface 106 which is formed substantially perpendicular to the principal surface 102 of the acrylic plate 100 to detect the defect of the acrylic plate 100. In the first embodiment, the acrylic plate 100 is used as an optical guide plate for the optical application such as a display. The acrylic plate 100, which is substantially rectangular and which has a thickness t, is used.

The light beam 104 predominantly including the nonparallel rays is introduced into the acrylic plate 100 by using a light source unit 114 comprising a light source array 110 (see FIG. 7) including a plurality of light sources 108 arranged along the side surface 106 of the acrylic plate 100, and a reflector (reflecting plate) 112 for covering the light source array 110.

That is, as shown in FIGS. 6 and 7, the light source array 110 is installed to oppose to one side surface 106 of the acrylic plate 100, and the light source array 110 is covered with the reflector 112. In this embodiment, for example, a reflector unit 118 is used, in which a U-shaped groove is formed in the longitudinal direction on one side surface of a housing member 116 formed of synthetic resin to have a columnar configuration, and the reflector 112 is formed along the groove.

Accordingly, the route for introducing the light into the side surface 106 of the acrylic plate 100 includes a route for directly introducing the light from the light source array 110, and a route for introducing the light supplied from the light source array 110 and reflected by the reflector 112. The light flux group, which is introduced via the foregoing routes into the acrylic plate 100, has a variety of angles of incidence.

In other words, the light source unit 114 functions as a light source for producing the group of light fluxes (light flux group) introduced into the side surface 106 of the acrylic plate 100 at various angles, i.e., the light beam predominantly including the non-parallel rays.

Figure 1:
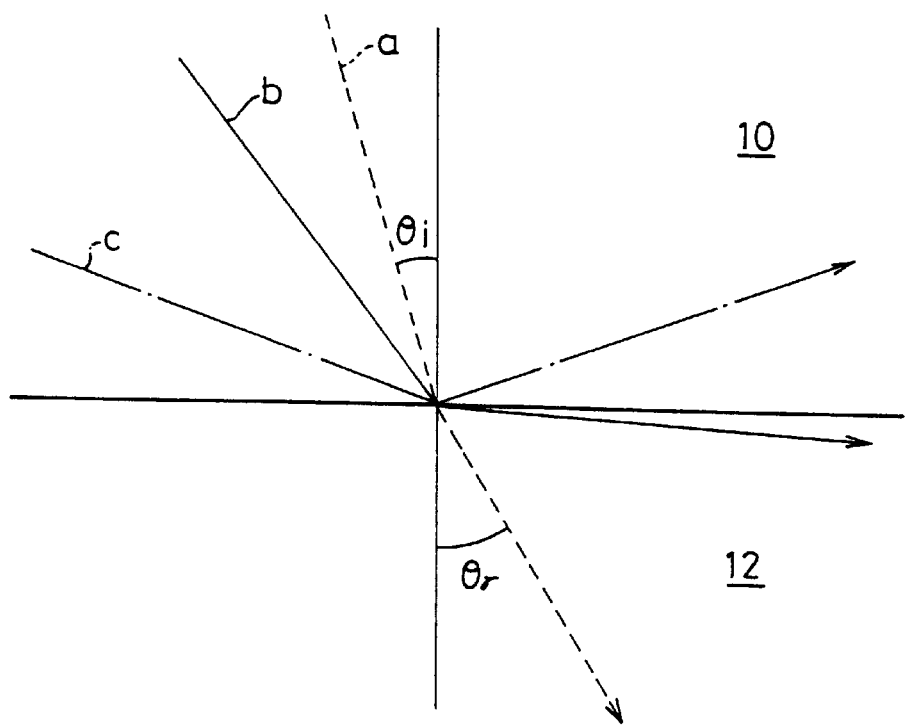
FIG. 1 illustrates the state of refraction of light, obtained when the light is transmitted from a transparent body as a detection objective to an air layer, concerning the method for detecting a defect of the transparent body according to i present invention.
Figure 2:
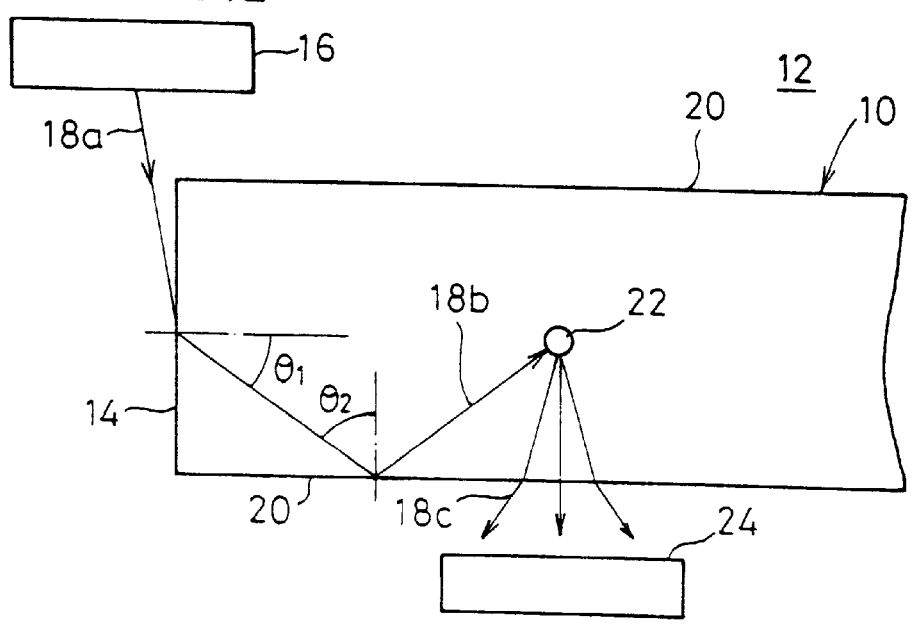
FIG. 2 illustrates the principle of the detection of the defect including, for example, a bubble, foreign matter in the transparent body, and a surface scratch, concerning the method for detecting the defect of the transparent body according to the present invention.

The light beam 104 predominantly including the non-parallel rays, which is introduced through the side surface 106 of the acrylic plate 100, is transmitted as follows as described in the explanation of the principle based on FIG. 2 as well, in accordance with the mutual relationship between the refractive indexes of the air and the acrylic plate 100. That is, if the acrylic plate 100 has no defect, then the introduced light beam 104 predominantly including the non-parallel rays is not leaked to the outside (in the outward direction of the acrylic plate 100), and is transmitted at the inside of acrylic plate 100 while being totally reflected by the front and back surfaces of the acrylic plate 100.

If any defect (for example, the bubble or the foreign matter) 120 exists in the acrylic plate 100, then the light beam 104 predominantly including the non-parallel rays introduced into the acrylic plate 100 is scattered, for example, by the bubble or the foreign matter 120, and it is leaked as the transmitted light 122 to the outside of the acrylic plate 100. The light scattering phenomenon also occurs at the edge of the foreign matter (object adhered to the surface) 124 adhered to the front and back surfaces of the acrylic plate 100 and at the scratch formed on the front and back surfaces of the acrylic plate 100.

Therefore, a light-receiving device 126 is arranged over the acrylic plate 100 such that its light-receiving surface 126a is opposed to the principal surface 102 of the acrylic plate 100. Thus, the bubble, the foreign matter or the like 120 existing at the inside of the acrylic plate 100 as well as the scratch and the foreign matter 124 adhered to the front and back surfaces of the acrylic plate 100 can be detected easily and quantitatively by measuring the light amount by using the light-receiving device 126.

In this case, the group of light fluxes having various angles are radiated onto and scattered by the bubble, foreign matter or the like 120, the object 124 adhered to the surface and the surface scratch. Therefore, it is possible to greatly improve the detection sensitivity for these defects.

The light-receiving device 126 is constructed such that it may be subjected to movement, for example, raster scanning in the superficial direction with respect to the principal surface of the acrylic plate 100 by using, for example, a known robot hand or the like. Thus, the defect can be easily detected over the entire surface of the acrylic plate 100. When the image processing is employed in combination, it is possible to easily recognize the position at which the defect exists.

Figure 3:
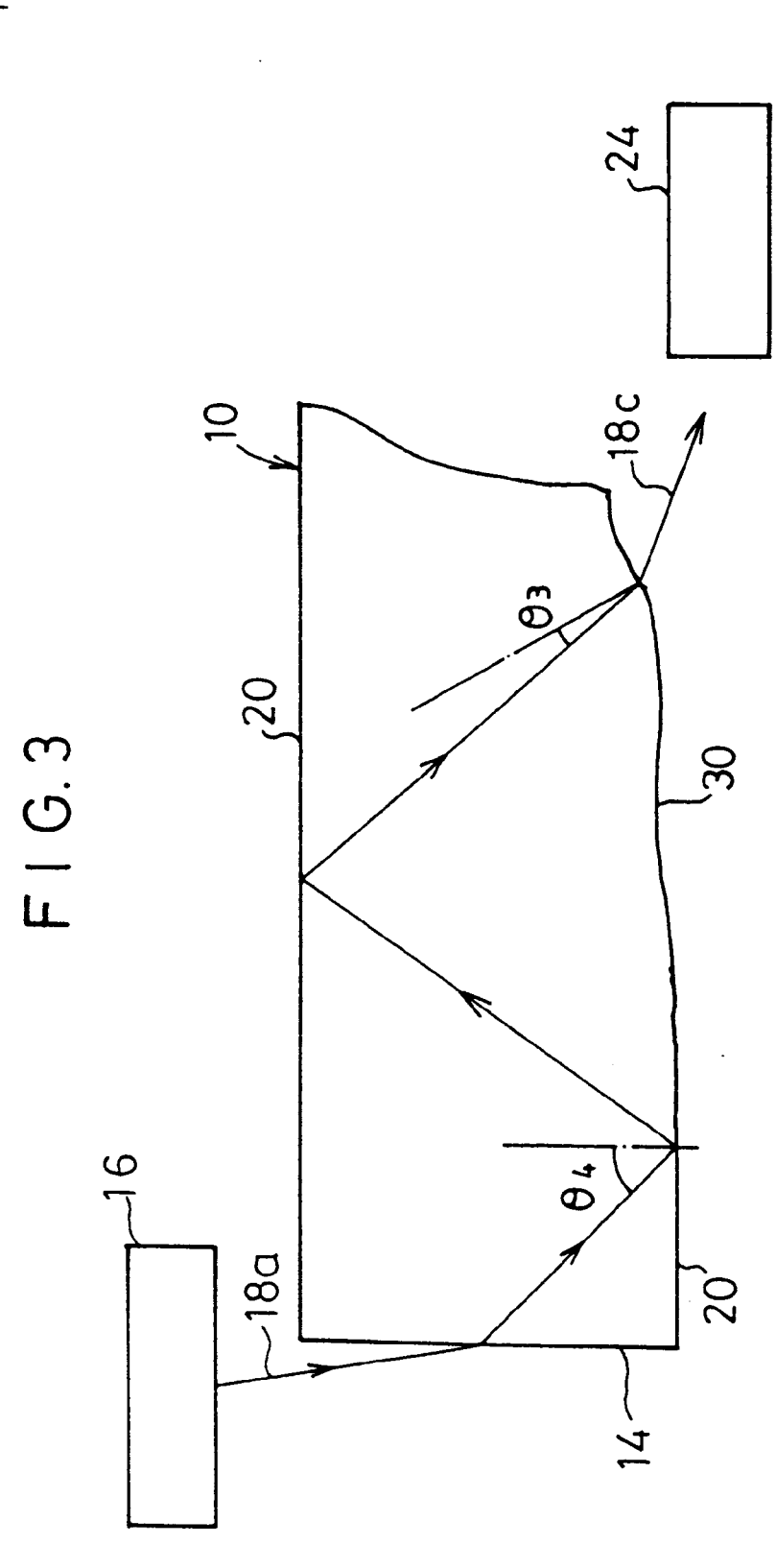
FIG. 3 illustrates the principle of the detection of the waviness of the transparent body itself, concerning the method for detecting the defect of the transparent body according to the present invention.
Figure 4:
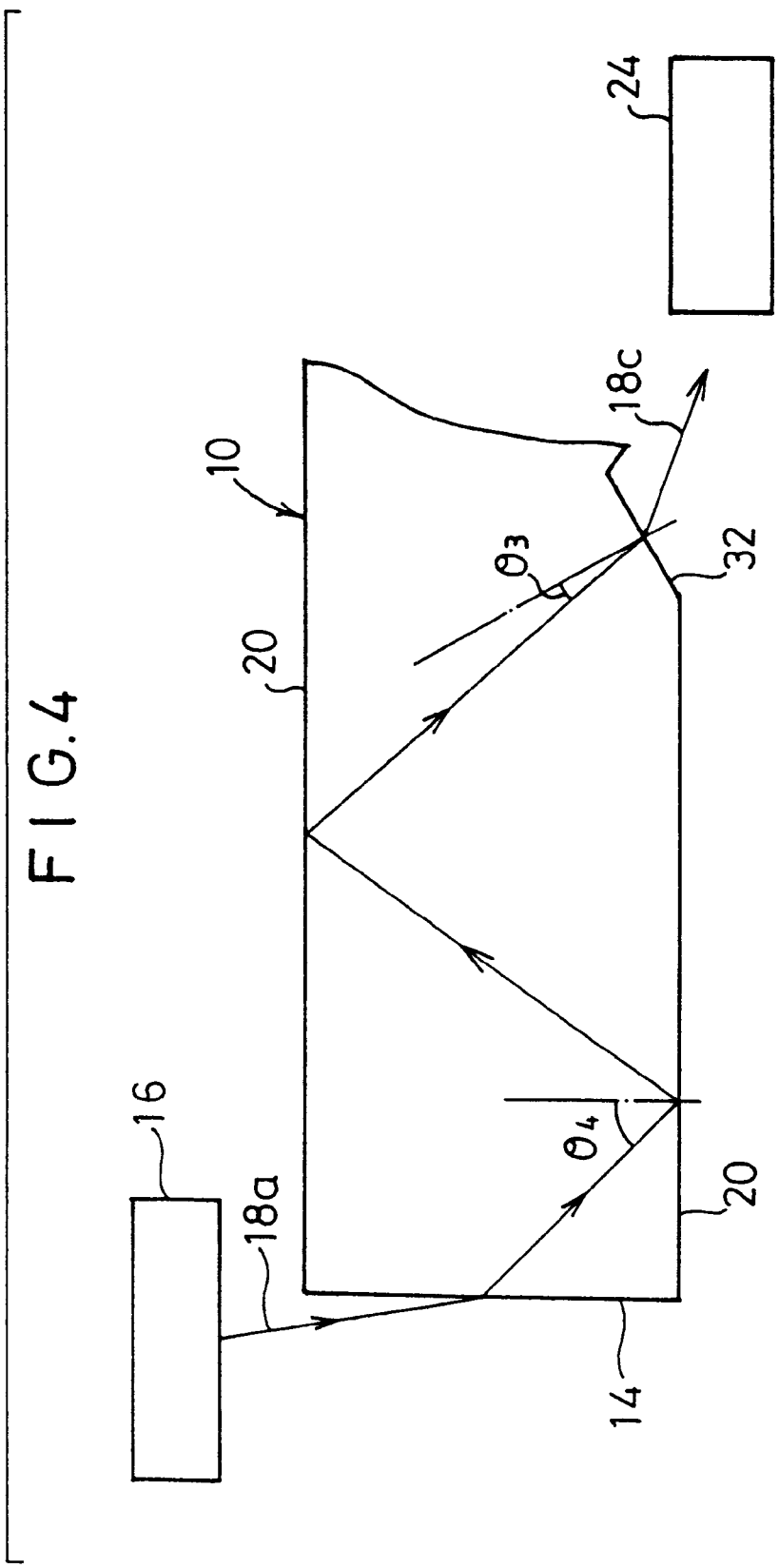
FIG. 4 illustrates the principle of the detection of a surface scratch, warpage, or the like of the transparent body itself, concerning the method for detecting the defect of the transparent body according to the present invention.
Figure 5:
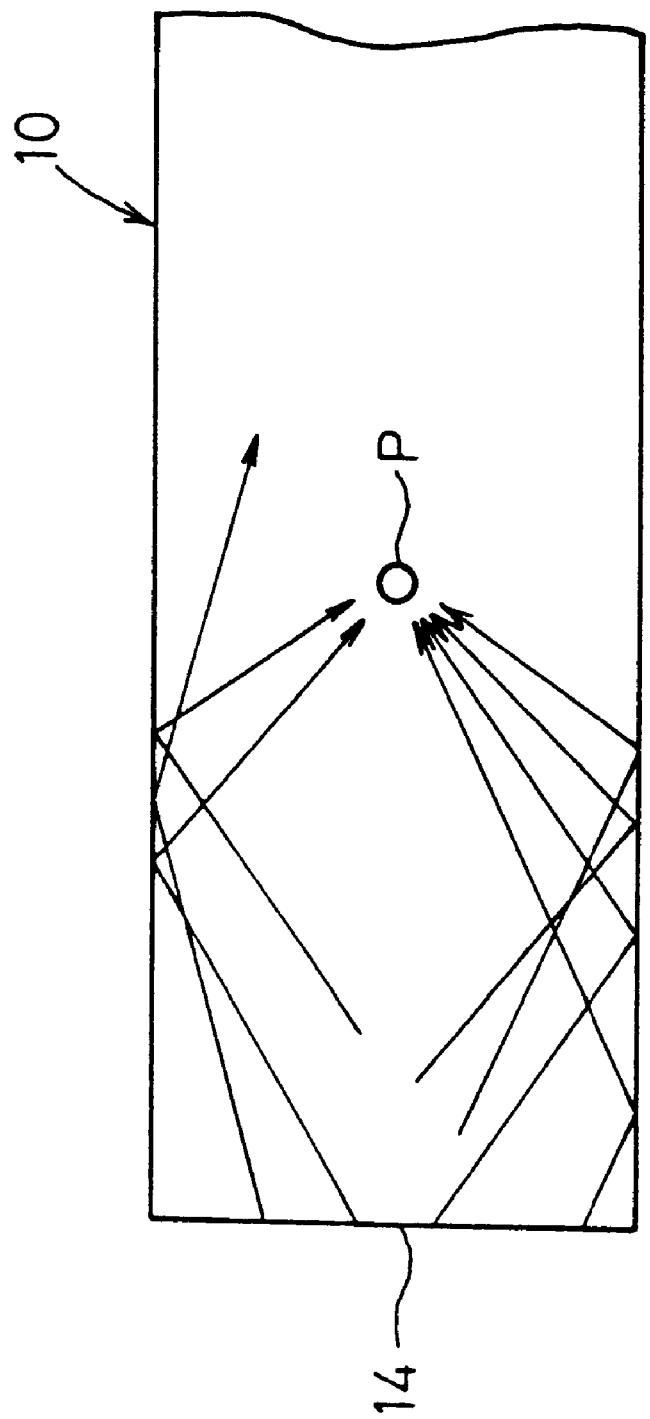
FIG. 5 illustrates the non-parallel rays, concerning the method for detecting the defect of the transparent body according to the present invention.

Further, the method for detecting the defect according to the first embodiment is not limited to the ability to detect the bubble, the foreign matter or the like 120 at the inside of the acrylic plate 100 as well as the surface scratch and the object 124 adhered to the surface of the acrylic plate. The method also makes it possible to easily detect, for example, the bend, the waviness, and the warpage of the acrylic plate 100 itself, as described in the explanation of the principle with reference to FIGS. 3 and 4 as well.

Specifically, as shown in FIG. 6, if the acrylic plate 100 involves a wavy surface 130, the light beam 104 predominantly including the non-parallel rays introduced into the acrylic plate 100 is leaked as the transmitted light 132 at the wavy surface 130 to the outside of the acrylic plate 100, especially in the direction toward the side surface 134 disposed on a side opposite to the side surface 106 at which the light source unit 114 is installed so that the transmitted light 132 travels substantially along the principal surface 102 of the acrylic plate 100. The phenomenon of light transmittance also occurs at bend portions and warpage portions of the acrylic plate 100.

Therefore, the light-receiving device 136 is arranged in the vicinity of the side surface 134 of the acrylic plate 100 such that its light-receiving surface 136a is substantially perpendicular to the principal surface of the acrylic plate 100. Thus, the defect of the acrylic plate 100 itself including, for example, the bend, the waviness, and the warpage can be detected easily and quantitatively by measuring the light amount by using the light-receiving device 136.

Also in this case, the group of light fluxes having various angles are radiated onto and scattered by the wavy surface 130, the bend portion, and the warpage portion. Therefore, it is possible to greatly improve the detection sensitivity for these defects.

The light-receiving device 136 is constructed such that it may be moved along the side surface 134 of the acrylic plate 100 by using, for example, a known robot hand or the like. Thus, it is possible to easily detect the defect such as the bend, the waviness, and the warpage of the acrylic plate 100 itself.

The light-receiving device 126 having the light-receiving surface 126a arranged opposingly to the principal surface of the acrylic plate 100 is provided in combination with the light-receiving device 136 having the light-receiving surface 136a arranged substantially perpendicularly to the principal surface of the acrylic plate 100. Thus, the bubble, the foreign matter or the like 120 at the inside of the acrylic plate 100 and the object 124 adhered to the surface and the surface scratch of the acrylic plate 100 can be detected simultaneously with the detection of the bend, the waviness, and the warpage of the acrylic plate 100 itself. Therefore, it is possible to greatly shorten the time required to detect the defect.

As described above, the method for detecting the defect according to the first embodiment is the defect-detecting method which utilizes the total reflection at the front and back surfaces of the acrylic plate 100. The foreign matter, the bubble, the scratch, the waviness, the warpage and the like, which exist at the inside and on the front and back surfaces of the acrylic plate 100, can be simultaneously detected. Further, it is unnecessary to produce any parallel light. Therefore, the detection of the defect can be realized by using the simple apparatus construction.

Figure 8A:
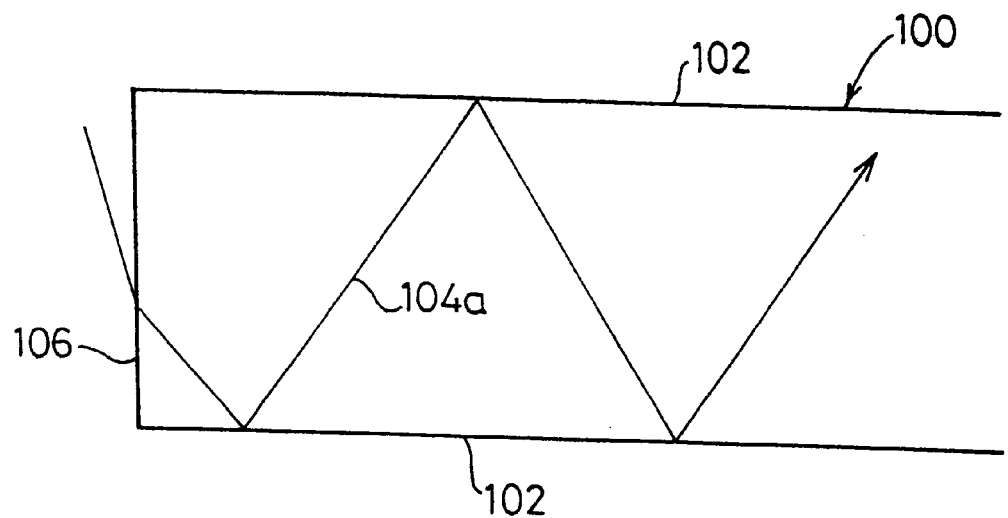
FIG. 8A illustrates the action of the light flux group introduced into the acrylic plate substantially in parallel to the side surface of the acrylic plate.

As shown in FIG. 8A, the light flux group 104a introduced into the acrylic plate 100 substantially in parallel to the side surface 106, which is included in the light beam 104 predominantly including the non-parallel rays radiated from the light source unit 114, is reflected many times at the inside of the acrylic plate 100. Therefore, the detection sensitivity is improved for any of the defects such as the foreign matter, the bubble, the scratch, the waviness, and the warpage which exist at the inside and on the front and back surfaces of the acrylic plate 100.

If the light flux group introduced into the acrylic plate 100 includes only the light flux group 104a introduced substantially in parallel to the side surface 106 as described above, it is impossible to introduce a sufficient amount of light into the middle portion of the acrylic plate 100, because the light is transmitted due to the defect at the inside of the acrylic plate 100 especially in the case of the detection of the defect of the acrylic plate having a large size (for example, an acrylic plate used for the aquarium).

Figure 8B:
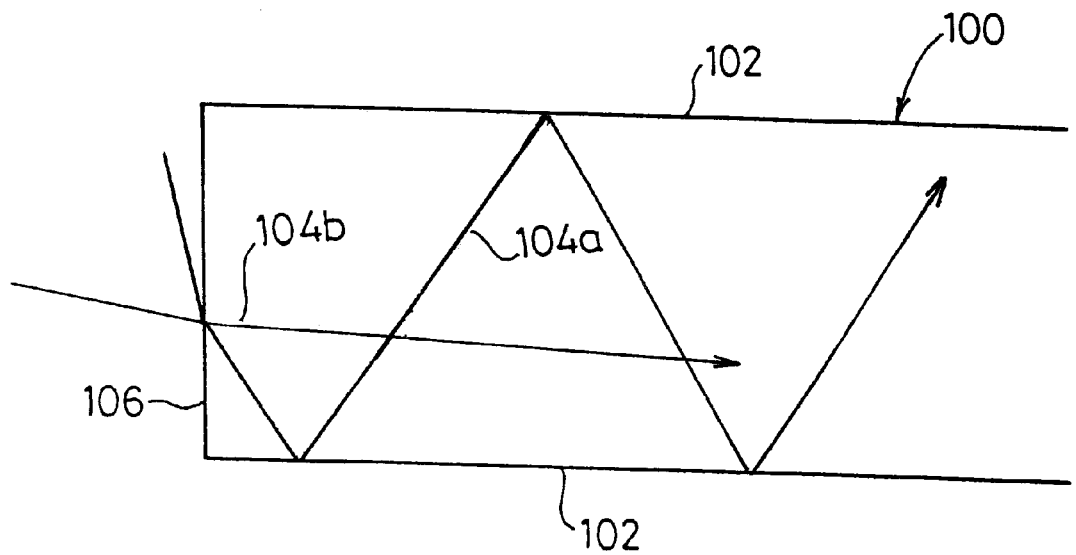
FIG. 8B illustrates the action of the light flux group introduced into the acrylic plate substantially in parallel to the principal surface of the acrylic plate.

However, as shown in FIG. 8B, the light beam 104 predominantly including the non-parallel rays in the first embodiment also includes the light flux group 104b parallel to the principal surface of the acrylic plate 100 (to be introduced into the portions separated far from the light source) in addition to the light flux group 104a as described above. Therefore, the shortage in light amount as described above does not occur. It is possible to introduce a substantially constant amount of light over the entire acrylic plate 100. Thus, it is possible to improve the sensitivity of the defect detection over the entire acrylic plate 100. In this arrangement, the sufficient ratio of the nonparallel rays is not less than 50%. More preferably, the ratio of the non-parallel rays is not less than 90%.

Each of the light sources 108 for constructing the light source array 110 of the light source unit 114 is not specifically limited provided that the light beam 104 predominantly including the non-parallel rays is radiated. Those usable as the light source 108 include, for example, fluorescent tubes, metal halide lamps, xenon lamps, halogen lamps, incandescent lamps, and LED's. The size of the light source 108, especially its height h, is preferably not more than the thickness t of the acrylic plate 100. In order to introduce the light beam 104 dominantly including the nonparallel rays having many angles of incidence in an amount as large as possible, the light beam 104 is preferably introduced through the entire end surface of the acrylic plate 100.

The shape of the acrylic plate 100 is not specifically limited. That is, the principal surface of the acrylic plate 100 may have a circular, rectangular, elliptic, or polygonal planar configuration. Alternatively, the planar configuration may be a combination of these configurations. However, it is necessary that the side surface 106, through which the light beam is introduced, be substantially perpendicular to the principal surface 102. Desirably, it is preferable that all of the side surfaces (106, 134, 140, 142, see FIG. 7) of the acrylic plate 100 are substantially perpendicular to the principal surface 102 of the acrylic plate 100.

Further, a reflector (conveniently referred to as "end surface reflector") 144 may be provided on the side surfaces 134, 140, 142 other than the side surface 106 for which the light source unit 114 is installed, of the side surfaces (106, 134, 140, 142) of the acrylic plate 100. In this arrangement, the light flux group, which arrives at the side surface 134, is reflected by the end surface reflector 144, and it is introduced again into the inside of the acrylic plate 100. Therefore, even when the amount of light introduced from the light source unit 114 is constant, it is possible to further improve the detection sensitivity for the defect, and it is also possible to improve the detection accuracy for the defect (existing size of the defect).

Figure 10A:
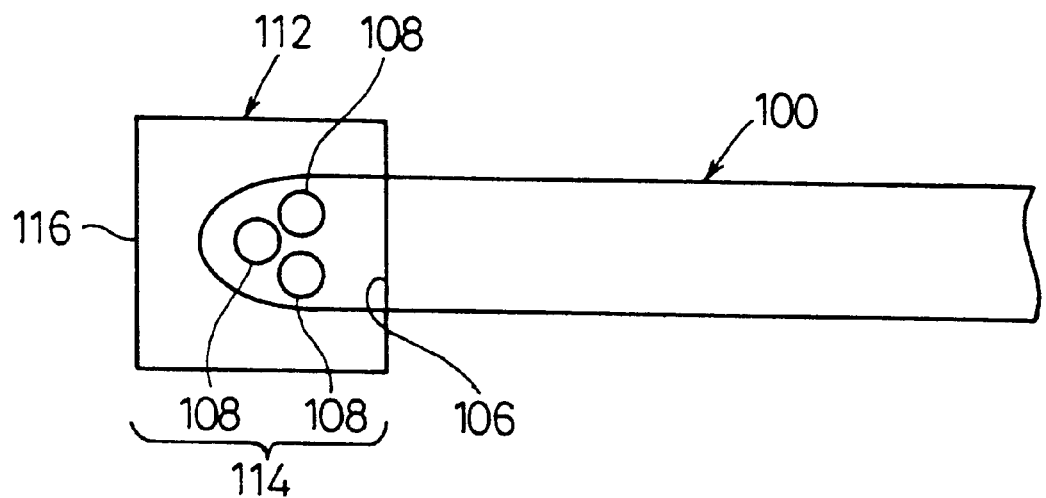
FIG. 10A shows a side arrangement of an embodiment based on the use of a plurality of fluorescent tubes as light sources.
Figure 10B:
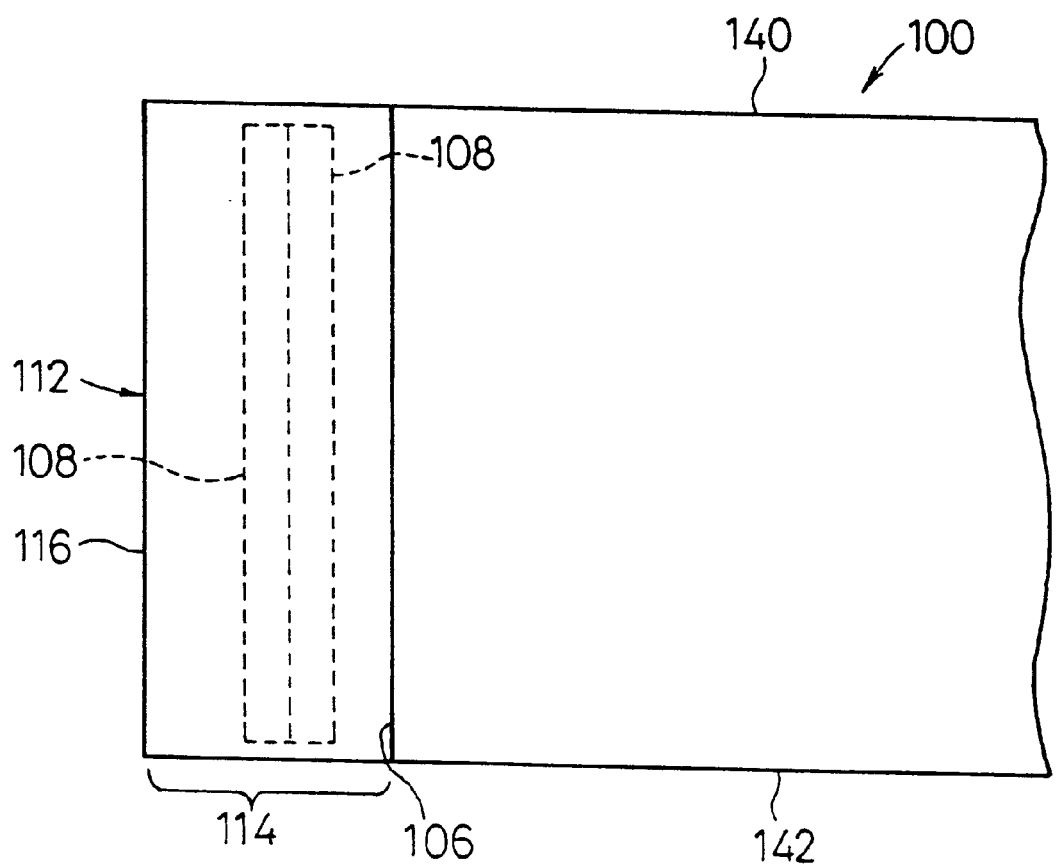
FIG. 10B shows a planar arrangement of an embodiment based on the use of a plurality of fluorescent tubes as light sources.

In the first embodiment described above, the light source array 110 is constructed by arranging the plurality of light sources 108 along the side surface 106 of the acrylic plate 100. Alternatively, as shown in FIG. 9, when a slender and cylindrical fluorescent tube is used as the light source 108, for example, one fluorescent tube 108 may be arranged with its axial direction being directed along the side surface of the acrylic plate 100. Of course, as shown in FIGS. 10A and 10B, a plurality of fluorescent tubes 108 may be aligned along the side surface of the acrylic plate 100.

The first embodiment is illustrative of the case in which the light source unit 114 is provided at one position. However, as in a method for detecting the defect according to the second embodiment shown in FIG. 11, the light source unit 114 may be provided on two side surfaces (side surfaces 106, 142 in the embodiment shown in FIG. 11) with one corner interposed therebetween. In this embodiment, it is preferable that the end surface reflector 144 is also provided at two positions. Accordingly, a substantially constant amount of light can be efficiently introduced into the entire acrylic plate 100. Thus, it is possible to further improve the sensitivity of the defect detection for the entire acrylic plate 100, and it is also possible to improve the detection accuracy for the defect (existing size of the defect).

In an experiment, a visible region light emitting diode (LED) was used as the light source 108 shown in FIG. 6. Luminance meters were used as the two types of light-receiving devices 126, 136 respectively. The respective devices were connected to an unillustrated appropriate power source.

The visible region light emitting diode (LED) for constructing the light source 108 is not specifically limited for the color of emitted light. However, for example, a green color light emitting diode (NSPG 500S produced by Nichia Chemical Industries, Ltd.) was used. For example, a J17 type luminance meter produced by Sony Tektronix Corporation equipped with a J1803 type luminance head was used as each of the luminance meters for constructing the light-receiving devices 126, 136.

With reference to FIG. 6, for example, explanation will be made for the function of the light flux component 104c radiated onto the side surface 106 of the acrylic plate 100 at an angle of incidence of 80°, of the light beam 104 predominantly including the non-parallel rays introduced from the light source unit 114 into the acrylic plate 100. The angle of refraction in the acrylic plate 100 concerning the light flux component 104c having the angle of incidence of 80° is 41.3° which is near to the critical angle of 42.2°.

When the light flux component 104c arrives at the principal surface 102 of the acrylic plate 100, the angle of incidence with respect to the air is 48.7° which exceeds the critical angle of 42.2°. Therefore, the light flux component 104c behaves as the reflected light beam at portions at which the principal surface 102 of the acrylic plate 100 is a completely smooth surface, and no transmitted light 122 is generated. However, for example, if the bubble or the foreign matter 120 exists at the inside of the acrylic plate 100, then the light flux component 104c is scattered by the bubble, foreign matter or the like 120, and the transmitted light 122 is generated. Accordingly, the transmitted light 122 is detected for its light amount by the luminance meter 126. Thus, it is possible to quantitatively recognize the defect such as the bubble and the foreign matter 120 and the defect of the unillustrated surface scratch.

In this case, the angle of incidence, which is used when the light of the visible region light emitting diode (LED) as the light source 108 is radiated onto the side surface 106 of the acrylic plate 100, may be an arbitrary angle from 0° to 90°.

The detection level obtained by the light-receiving device 126 is not necessarily subjected to relative comparison in a successful manner. The amount of light differs between places for the detection, for example, depending on the distribution of the existence of the defect in some cases. In the case of the acrylic plate 100 having a high light absorption rate, the light amount is decreased as the distance from the light source 108 becomes far. In such a case, the detection level is lowered at the light-receiving device 126, which appears as if few defects exist. The dependency of the detection level on the detection place is more conspicuous when the acrylic plate 100 has a larger area.

A method for detecting the defect according to the third embodiment, which solves the problem as described above, will be explained below with reference to FIGS. 12A to 13.

Figure 12A:
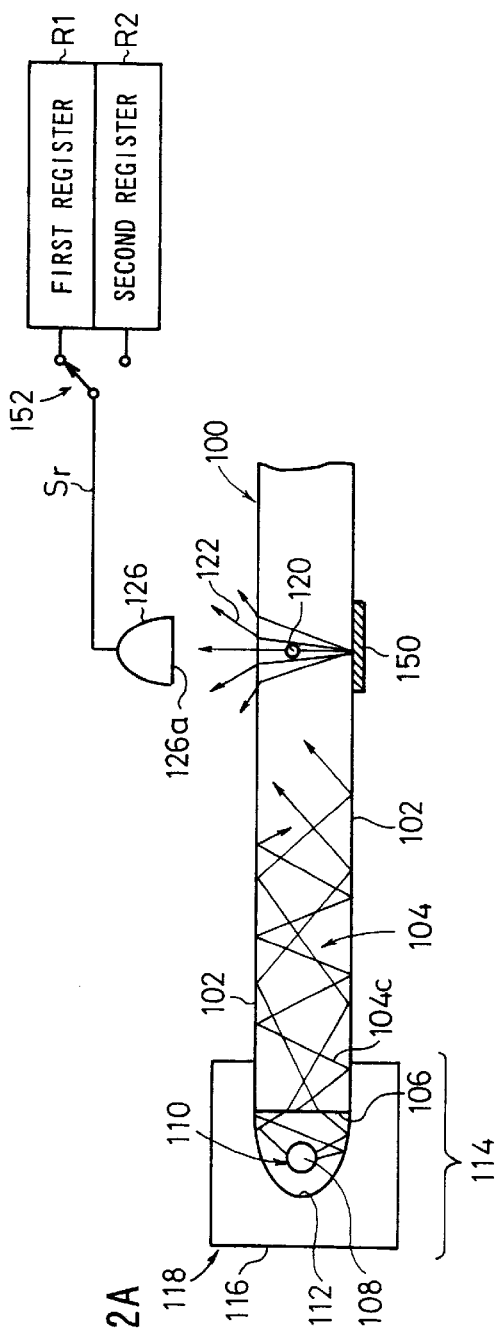
FIG. 12A illustrates the process for detecting the maximum level of the transmitted light by allowing a scattering member to make contact with a principal surface of an acrylic plate.
Figure 12B:
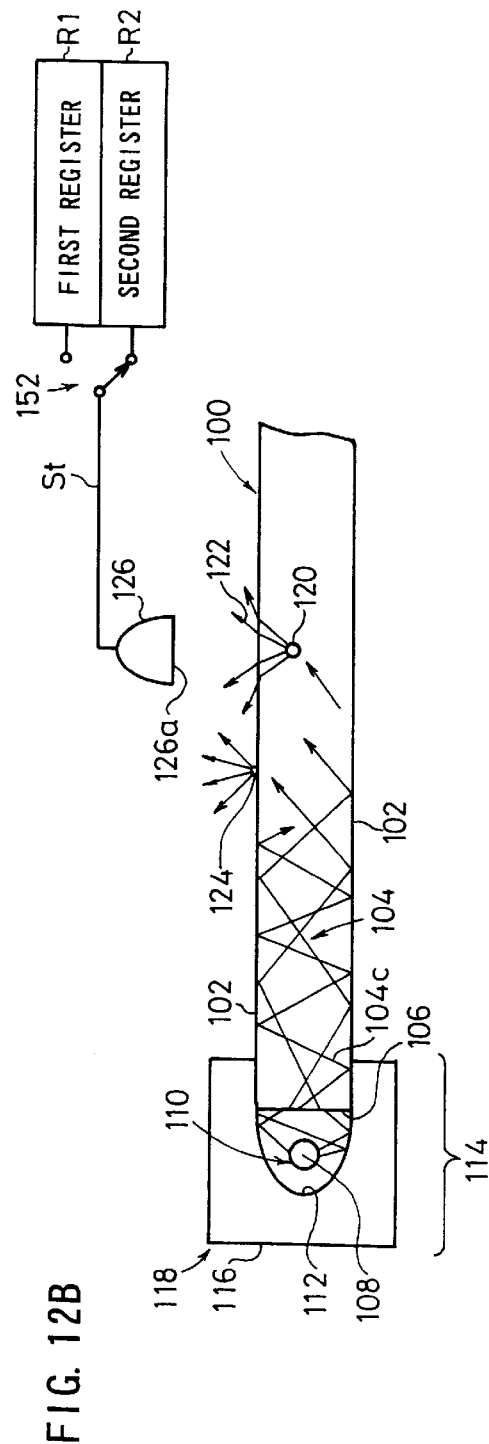
FIG. 12B illustrates the process for detecting the level of the transmitted light affected by the defect after removing the scattering member.

As shown in FIGS. 12A and 12B, the method for detecting the defect according to the third embodiment is constructed on the basis of approximately the same principle as that of the specified example of the method for detecting the defect according to the first embodiment described above (see FIG. 6). However, the former is different from the other in the following points.

At first, a scattering member 150 is allowed to make contact at a position opposite to the light-receiving surface 126a of the light-receiving device 126 on the principal surface on the side opposite to the side on which the light-receiving device 126 is arranged of the principal surfaces of the acrylic plate 100.

When the scattering member 150 is allowed to make contact with the acrylic plate 100, it is preferable that a liquid having a refractive index not less than the refractive index of the acrylic plate 100 is allowed to intervene, in order that the tight contact performance is secured for the contact of the scattering member 150, and that the light beam 104 from the light source 108 arrives at the scattering member 150 without causing any total reflection at the interface of the contact. For example, assuming that the refractive index of the acrylic plate 100 is 1.49, the liquid having a refractive index of not less than the refractive index of 1.49 is preferably used.

The transmitted light 122 obtained in this arrangement is detected by using the light-receiving device 126. An obtained detection level is designated as the reference level Sr which is stored in a first register R1 by the aid of a switching circuit 152. Those usable as the scattering member 150 include, for example, a green sheet of $TiO_2$.

The reference level Sr represents the maximum level at the position of the contact of the scattering member 150 concerning the acrylic plate 100. The reference level Sr is not affected by the presence or absence of the defect (for example, the bubble and the foreign matter) 120. However, the level changes depending on the detection place. That is, the reference level Sr is the maximum level depending on the detection place.

Subsequently, as shown in FIG. 12B, the scattering member 150 is removed, and the transmitted light 122 obtained in this arrangement Is detected by using the light-receiving device 126. The obtained detection level s is designated as the observation level St which is stored in a second register R2 by the aid of the switching circuit 152. The observation level St is the level corresponding to the existing size of the defect 120 detected by the light-receiving device 126. However, also In this case, the observation level St is the level depending on the detection place.

Figure 13:
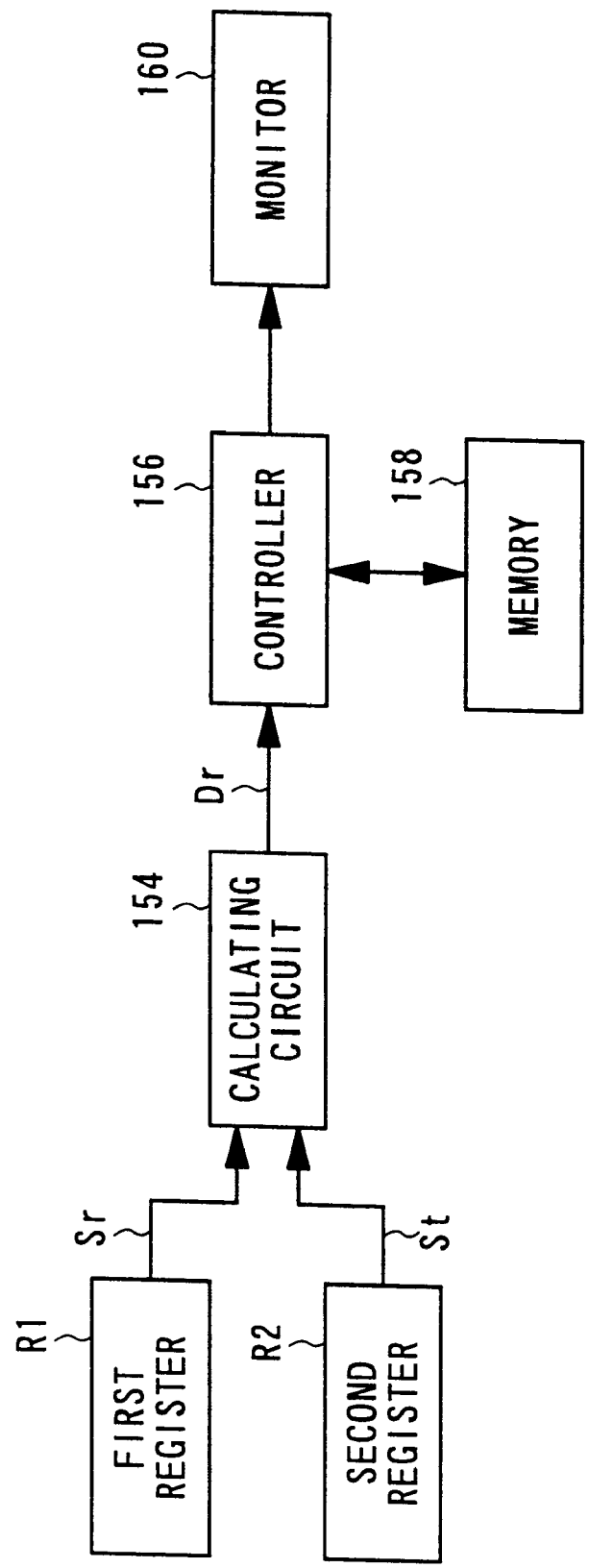
FIG. 13 shows a block diagram illustrating the data processing performed in accordance with the method for detecting the defect according to a third embodiment.

As shown in FIG. 13, the ratio (St/Sr) between the reference level Sr stored in the first register R.I. and the observation level St stored in the second register R2 is calculated by using a calculating circuit 154. An obtained calculation result (ratio data Dr) Is registered in a memory 158 by the aid of a controller 156. The ratio data Dr clearly expresses the degree of the observation level St at the relevant detection place with respect to the maximum level (reference level) Sr at the relevant detection place.

An array variable region is developed for the memory 158 corresponding to the coordinate at which the scattering member 150 is arranged with respect to the acrylic plate 100. The ratio data Dr is registered in an array variable region based on the coordinate information outputted from the apparatus for positioning the light-receiving device 126, or in an array variable region based on the coordinate of arrangement of the scattering member 150.

For example, pieces of the ratio data Dr, which are successively registered for the respective coordinates in the memory 158, are classified for the color for each of the levels to make display, for example, on a monitor 160 connected to the controller 156. Accordingly, the distribution of the existence of the defect for the acrylic plate 100 can be confirmed at a glance.

Especially when the acrylic plate 100 is used as an optical guide plate for a display, the contact and the removal of the scattering member 150 correspond to the contact and the separation of the picture element with respect to the optical waveguide plate as described, for example, in Japanese Laid-Open Patent Publication No. 10-78549. Therefore, the distribution of the existence of the defect can be detected by carrying out the method for detecting the defect according to the third embodiment described above, simultaneously with which the light emitting characteristics of the display (dispersion in luminance and contrast) can be confirmed.

In other words, the inspection for the defect can be performed for the optical guide plate simultaneously with the inspection for the light emission for adjusting the luminance for the unit of picture element. Thus, it is possible to simplify the inspection process. Further, the ratio data Dr registered in the memory 158 can be utilized for the coefficient data for adjusting the luminance for the unit of picture element. Thus, it is possible to improve the effective utilization of the data processing.

Figure 14:
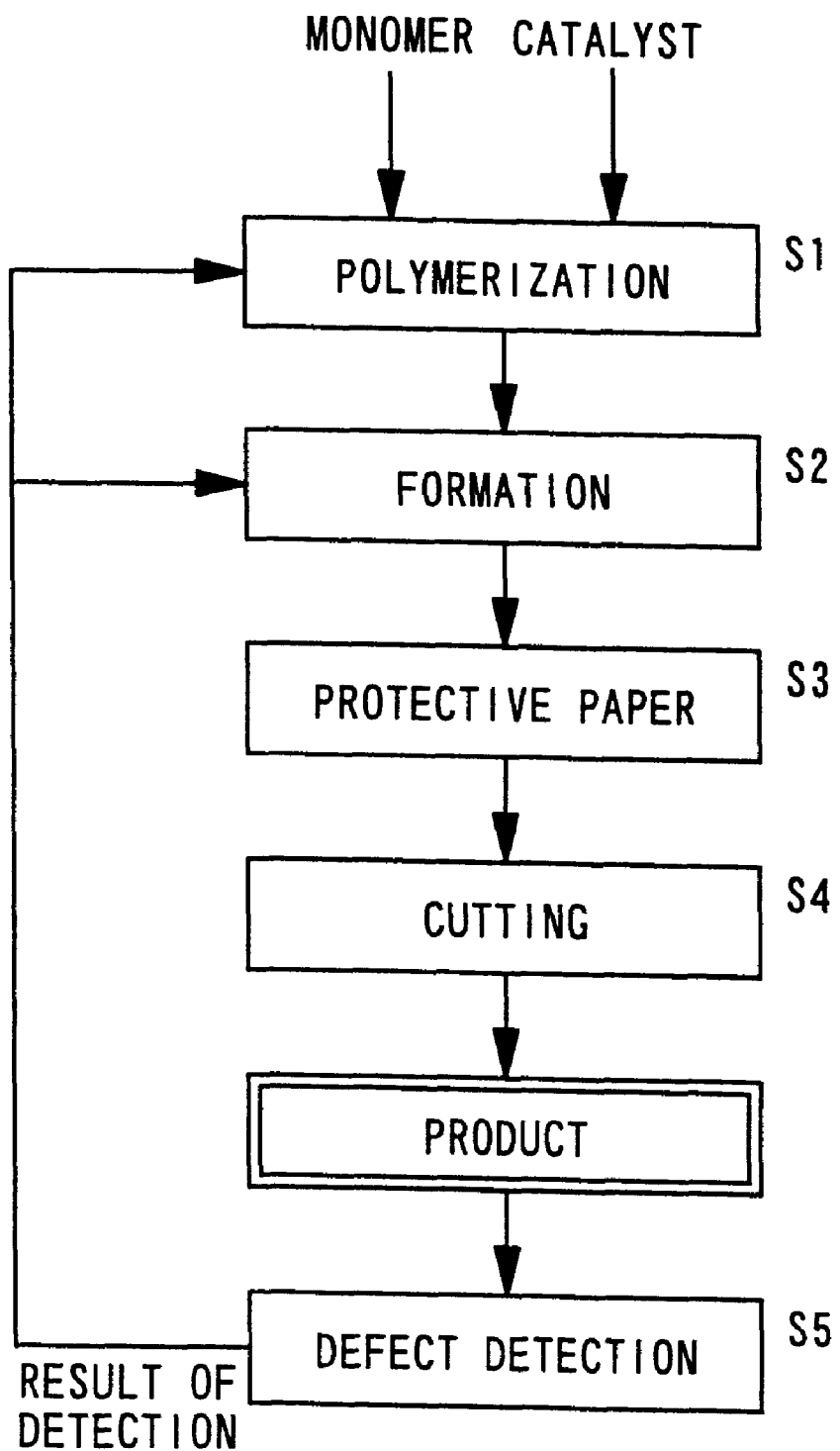
FIG. 14 shows a block diagram depicting the steps of the method for producing the acrylic plate.

In general, the acrylic plate 100 is produced in accordance with the production steps as shown in FIG. 14. That is, a monomer is polymerized and solidified by the aid of a catalyst (step S1), followed by formation into a band-shaped configuration or a plate-shaped configuration (step S2). An obtained formed product is covered with protective paper (step S3), followed by cutting (step S4) to obtain a completed product.

Usually, the product may be shipped as it is. However, it is preferable that the method for detecting the defect according to each of the first to third embodiments may be applied to the acrylic plate 100 as the product (step S5). The result of detection obtained by the method for detecting the defect is sent to the polymerization step and/or the forming step in a feedback manner to use in the polymerization process and/or the forming process. In this procedure, it is possible to produce the transparent body having fewer defects and having a high quality.

It is a matter of course that the method for detecting the defect of the transparent body and the method for producing the transparent body according to the present invention are not limited to the embodiments described above, which may be embodied in other various forms without deviating from the gist or essential characteristics of the present invention.

As explained above, according to the method for detecting the defect of the transparent body concerning the present invention, it is possible to accurately and quantitatively detect the defect of the transparent body including, for example, the surface scratch as well as the bubble, foreign matter, or the like existing inside of the transparent body. Further, it is possible to accurately and quantitatively detect, for example, the bend and the waviness of the transparent body itself. Furthermore, it is possible to perform the detection of the surface scratch of the transparent body as well as the bubble, foreign matter, or the like existing inside of the transparent body, simultaneously with the detection of the defect such as the bend and the waviness of the transparent body itself by using the identical optical system.

According to the method for producing the transparent body concerning the present invention, it is possible to send the result of the detection of the defect obtained as described above by the method for detecting the defect of the transparent body, to the production line for the transparent body in the feedback manner. Thus, it is possible to produce the transparent body having fewer defects and having a high quality.

What is claimed is:

1. A method for detecting a defect in a transparent body having two opposed principal surfaces and side surfaces substantially perpendicular to said principal surfaces, comprising:

assuming at least one imaginary point within said body at a position other than along a mid-point between said principal surfaces;

introducing a light beam into at least one side surface of said transparent body such that light passing through said imaginary point includes rays that are parallel and non-parallel to said principal surfaces; and detecting light rays reflected out of at least one of said principal surfaces to quantitatively detect defects in said transparent body.

2. The method according to claim 1, wherein transmitted light, which is obtained through said principal surface of said transparent body on the basis of said defect, is detected by using at least one light-receiving device with its light-receiving surface arranged and directed substantially in parallel to said principal surface of said transparent body to quantitatively detect an existing amount of said defect of said transparent body.

3. The method according to claim 2, wherein:

a scattering member is allowed to make contact at a position opposing to said light-receiving surface of said light-receiving device on said principal surface of said transparent body disposed on a side opposite to a side on which said light-receiving device is arranged to detect transmitted light in this arrangement by using said light-receiving device so that an obtained detection level is designated as a reference level;

transmitted light, which is obtained when said scattering member is removed, is detected by using said light-receiving device so that an obtained detection level is designated as an observation level; and a ratio between said reference level and said observation level is used to quantitatively detect said existing amount of said defect of said transparent body.

4. The method according to claim 1, wherein transmitted light, which is obtained through said principal surface of said transparent body on the basis of said defect, is detected by using at least one light-receiving device with its light-receiving surface arranged and directed substantially perpendicularly to said principal surface of said transparent body to quantitatively detect an existing amount of said defect of said transparent body.

5. The method according to claim 4, wherein said defect is one of bend, waviness, surface scratch, warpage, and loss of flatness.

6. The method according to claim 1, wherein transmitted light, which is obtained through said principal surface of said transparent body on the basis of said defect, is detected by using any one of or both of at least one light-receiving device with its light-receiving surface arranged and directed substantially in parallel to said principal surface of said transparent body and at least one light-receiving device with its light-receiving surface arranged and directed substantially perpendicularly to said principal surface of said transparent body to quantitatively detect an existing amount of said defect of said transparent body.

7. The method according to claim 6, wherein:

when said light-receiving device is arranged so that its light-receiving surface is directed substantially in parallel to said principal surface of said transparent body to detect said defect of said transparent body;

a scattering member is allowed to make contact at a position opposing to said light-receiving surface of said light-receiving device on said principal surface of said transparent body disposed on a side opposite to a side on which said light-receiving device is arranged to detect transmitted light in this arrangement by using said light-receiving device so that an obtained detection level is designated as a reference level;

transmitted light, which is obtained when said scattering member is removed, is detected by using said light-receiving device so that an obtained detection level is designated as an observation level; and a ratio between said reference level and said observation level is used to quantitatively detect said existing amount of said defect of said transparent body.

8. The method according to claim 6, wherein said defect is one of bend, waviness, surface scratch, warpage, and loss of flatness.

9. The method according to claim 8, wherein when said light-receiving device is arranged so that its light-receiving surface is directed substantially in parallel to said principal surface of said transparent body to detect said defect of said transparent body:

a scattering member is allowed to make contact at a position opposite to said light-receiving surface of said light-receiving device on said principal surface of said transparent body disposed on a side opposite to a side on which said light-receiving device is arranged to detect transmitted light in this arrangement by using said light-receiving device so that an obtained detection level is designated as a reference level;

transmitted light, which is obtained when said scattering member is removed, is detected by using said light-receiving device so that an obtained detection level is designated as an observation level; and a ratio between said reference level and said observation level is used to quantitatively detect said existing amount of said defect of said transparent body.

10. The method according to claim 1, wherein a light beam from a light source is used as said light beam dominantly including said non-parallel rays by the aid of a light source side reflector installed on a side of said light source, and it is introduced through said side surface of said transparent body.

11. The method according to claim 10, wherein said reflector is arranged for a side surface of said side surfaces of said transparent body other than said side surface for which said light source is installed.

12. The method according to claim 10, wherein an angle of incidence of said light beam from said light source with respect to said side surface of said transparent body is controlled by using said light source side reflector.

13. The method according to claim 1, wherein said light beam passing through said imaginary point includes said non-parallel rays in am amount not less than 50% of said light beam.

14. A method for detecting a defect in a transparent body having two opposed principal surfaces and side surfaces substantially perpendicular to said principal surfaces, comprising:

assuming at least one imaginary point within said body at a position other than along a mid-point between said principal surfaces;

introducing a light beam into at least one side surface of said transparent body such that light passing through said imaginary point includes rays that are parallel and non-parallel to said principal surfaces;

positioning at least one light-receiving device proximate a first one of said two opposed principal surfaces of said transparent body such that a light-receiving surface of said light-receiving device is substantially parallel to said first principal surface;

arranging a scattering member proximate a second of said two opposed principal surfaces of said transparent body;

contacting a portion of said second principal surface with said scattering member to emit light out of said first principal surface for detection by said light-receiving device, thereby obtaining a reference detection level;

removing said scattering member from contact with said second principal surface and detecting light emitted out of said first principal surface due to defects contained in said transparent body to thereby obtain an observation detection level; and calculating a ratio between said reference detection level and said observation detection level to detect quantitatively defects in said transparent body.

15. The method according to claim 14, wherein said defect of said transparent body is detected such that transmitted light, which is obtained through said principal surface of said transparent body on the basis of said defect, is detected by using at least one light-receiving device with its light-receiving surface arranged and directed substantially perpendicularly to said principal surface of said transparent body to quantitatively detect an existing amount of said defect of said transparent body.

16. The method according to claim 15, wherein said defect is one of bend, waviness, surface scratch, warpage, and loss of flatness.

17. The method according to claim 14, wherein said defect of said transparent body is detected such that transmitted light, which is obtained through said principal surface of said transparent body on the basis of said defect, is detected by using any one of or both of at least one light-receiving device with its light-receiving surface arranged and directed substantially in parallel to said principal surface of said transparent body and at least one light-receiving device with its light-receiving surface arranged and directed substantially perpendicularly to said principal surface of said transparent body to quantitatively detect an existing amount of said defect of said transparent body.

18. The method according to claim 17, wherein:

when said light-receiving device is arranged so that its light-receiving surface is directed substantially in parallel to said principal surface of said transparent body to detect said defect of said transparent body;

a scattering member is allowed to make contact at a position opposing to said light-receiving surface of said light-receiving device on said principal surface of said transparent body disposed on a side opposite to a side on which said light-receiving device is arranged to detect transmitted light in this arrangement by using said light-receiving device so that an obtained detection level is designated as a reference level;

transmitted light, which is obtained when said scattering member is removed, is detected by using said light-receiving device so that an obtained detection level is designated as an observation level; and a ratio between said reference level and said observation level is used to quantitatively detect said existing amount of said defect of said transparent body.

19. The method according to claim 17, wherein said defect is one of bend, waviness, surface scratch, warpage, and loss of flatness.

20. The method according to claim 19, wherein when said light-receiving device is arranged so that its light-receiving surface is directed substantially in parallel to said principal surface of said transparent body to detect said defect of said transparent body:

a scattering member is allowed to make contact at a position opposite to said light-receiving surface of said light-receiving device on said principal surface of said transparent body disposed on a side opposite to a side on which said light-receiving device is arranged to detect transmitted light in this arrangement by using said light-receiving device so that an obtained detection level is designated as a reference level;

transmitted light, which is obtained when said scattering member is removed, is detected by using said light-receiving device so that an obtained detection level is designated as an observation level; and a ratio between said reference level and said observation level is used to quantitatively defect said existing amount of said defect of said transparent body.

21. The method according to claim 14, wherein said defect of said transparent body is detected such that a light beam from a light source is used as said light beam dominantly including said non-parallel rays by the aid of a light source side reflector installed on a side of said light source, and it is introduced through said side surface of said transparent body.

22. The method according to claim 21, wherein said reflector is arranged for a side surface of said side surfaces of said transparent body other than said side surface for which said light source is installed.

23. The method according to claim 21, wherein an angle of incidence of said light beam from said light source with respect to said side surface of said transparent body is controlled by using said light source side reflector.

* * * * *